(12) United States Patent
Dang et al.

(10) Patent No.: US 8,440,846 B2
(45) Date of Patent: May 14, 2013

(54) DIRECT EPOXIDATION PROCESS

(75) Inventors: Vu A. Dang, Bear, DE (US); Roger A. Grey, West Chester, PA (US); Jay F. Miller, Chester Springs, PA (US); Beaven S. Mandimutsira, Wynnewood, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 251 days.

(21) Appl. No.: 12/894,626

(22) Filed: Sep. 30, 2010

(65) Prior Publication Data

US 2012/0083612 A1 Apr. 5, 2012

(51) Int. Cl.
*C07D 301/06* (2006.01)
*C07D 301/12* (2006.01)

(52) U.S. Cl.
USPC .......................................... 549/533; 549/531

(58) Field of Classification Search .................. 549/533, 549/531
See application file for complete search history.

(56) References Cited

U.S. PATENT DOCUMENTS

| | | |
|---|---|---|
| 4,859,785 A | 8/1989 | Bellussi et al. |
| 4,883,260 A | 11/1989 | Kanda |
| 4,937,216 A | 6/1990 | Clerici et al. |
| 5,581,000 A | 12/1996 | Rodriguez et al. |
| 5,859,265 A | 1/1999 | Müller et al. |
| 5,965,754 A | 10/1999 | Clark et al. |
| 6,005,123 A | 12/1999 | Dessau et al. |
| 6,008,388 A | 12/1999 | Dessau et al. |
| 6,399,794 B1 | 6/2002 | Hancu |
| 6,498,259 B1 | 12/2002 | Grey et al. |
| 6,555,493 B2 | 4/2003 | Cooker et al. |
| 6,759,540 B2 | 7/2004 | Oguchi et al. |
| 7,030,255 B2 | 4/2006 | Grey et al. |
| 7,153,986 B2 | 12/2006 | Abekawa et al. |
| 7,531,674 B2 | 5/2009 | Ishino et al. |
| 2009/0054670 A1 | 2/2009 | Kawabata et al. |
| 2009/0054870 A1 | 2/2009 | Sharkey et al. |

FOREIGN PATENT DOCUMENTS

| | | |
|---|---|---|
| BE | 1001038 | 6/1989 |
| JP | 04-352771 | 7/1992 |
| WO | 2008156205 | 12/2008 |

OTHER PUBLICATIONS

PCT International Search Report and Written Opinion, dated Jan. 25, 2011, corresponding to PCT Serial No. PCT/US/2009/054003.
Wu et al., "A Novel Titanosilicate with MWW Structure. I. Hydrothermal Synthesis, Elimination of Extraframework Titanium and Characterizations, " Journal of Physical Chemistry B, 105, (2001), p. 2897-2905.

*Primary Examiner* — Taylor Victor Oh

(57) ABSTRACT

The invention is a process for epoxidizing an olefin with hydrogen and oxygen in a solvent comprising acetonitrile in the presence of an quinone-acid salt and a catalyst comprising a titanium zeolite and a noble metal. The process results in higher productivity and improved selectivity to propylene oxide from hydrogen and oxygen, as compared to processes that use only a quinone.

12 Claims, No Drawings

DIRECT EPOXIDATION PROCESS

FIELD OF THE INVENTION

This invention relates to a process for producing an epoxide by the reaction of an olefin, oxygen, and hydrogen.

BACKGROUND OF THE INVENTION

Many different methods for the preparation of epoxides have been developed. Generally, epoxides are formed by the reaction of an olefin with an oxidizing agent in the presence of a catalyst. Ethylene oxide is commercially produced by the reaction of ethylene with oxygen over a silver catalyst. Propylene oxide is commercially produced by reacting propylene with an organic hydroperoxide oxidizing agent, such as ethylbenzene hydroperoxide or tert-butyl hydroperoxide. This process is performed in the presence of a solubilized molybdenum catalyst or a heterogeneous titania on silica catalyst.

Besides oxygen and alkyl hydroperoxides, hydrogen peroxide is also a useful oxidizing agent for epoxide formation. U.S. Pat. No. 5,581,000 discloses a sulfonic acid-substituted anthrahydroquinone alkylammonium salt, and its use in the production of hydrogen peroxide. U.S. Pat. Nos. 4,833,260, 4,859,785, and 4,937,216, for example, disclose olefin epoxidation with hydrogen peroxide in the presence of a titanium silicate catalyst. U.S. Pat. Nos. 7,153,986 and 7,531,674 describe the epoxidation of propylene with hydrogen peroxide in the presence of an organic solvent and a crystalline titanosilicate catalyst having an MWW structure.

Much current research is conducted in the direct epoxidation of olefins with oxygen and hydrogen. In this process, it is believed that oxygen and hydrogen react in situ to form an oxidizing agent. Many different catalysts have been proposed for use in the direct epoxidation process. Typically, the catalyst comprises a noble metal and a titanosilicate. For example, JP 4-352771 discloses the formation of propylene oxide from propylene, oxygen, and hydrogen using a catalyst containing a Group VIII metal such as palladium on a crystalline titanosilicate. The Group VIII metal is believed to promote the reaction of oxygen and hydrogen to form a hydrogen peroxide in situ oxidizing agent. U.S. Pat. No. 6,498,259 describes a catalyst mixture of a titanium zeolite and a supported palladium complex, where palladium is supported on carbon, silica, silica-alumina, titania, zirconia, and niobia. Other direct epoxidation catalyst examples include gold supported on titanosilicates, see for example PCT Intl. Appl. WO 98/00413.

One disadvantage of the described direct epoxidation catalysts is that they are prone to produce non-selective byproducts such as glycols or glycol ethers formed by the ring-opening of the epoxide product or alkane byproduct formed by the hydrogenation of olefin. U.S. Pat. No. 6,008,388 teaches that the selectivity for the direct olefin epoxidation process is enhanced by the addition of a nitrogen compound such as ammonium hydroxide to the reaction mixture. U.S. Pat. No. 6,399,794 teaches the use of ammonium bicarbonate modifiers to decrease the production of ring-opened byproducts.

U.S. Pat. No. 6,005,123 teaches the use of phosphorus, sulfur, selenium or arsenic modifiers such as triphenylphosphine or benzothiophene to decrease the formation of unwanted propane. U.S. Pat. Appl. Pub. No. 2009/0054670 discloses a process for producing epoxides comprising reacting an olefin, oxygen and hydrogen in a liquid phase in the presence of a titanosilicate and a quinoid compound or a dihydro-form of quinoid, such as phenanthraquinone. WO2008/156205 teaches a method for producing propylene oxide comprising reacting propylene, oxygen, and hydrogen in the presence of a noble metal catalyst and a titanosilicate in the liquid phase containing a polycyclic compound.

As with any chemical process, it is desirable to attain still further improvements in the epoxidation methods. We have discovered a new process for the epoxidation of olefins.

SUMMARY OF THE INVENTION

The invention is an olefin epoxidation process that comprises reacting an olefin, oxygen, and hydrogen in a solvent comprising acetonitrile in the presence of a quinone-acid salt and a catalyst comprising a titanium zeolite and a noble metal. This process surprisingly gives higher productivity and improved propylene oxide selectivity from hydrogen and oxygen as compared to processes that use only a quinone.

DETAILED DESCRIPTION OF THE INVENTION

The process of the invention comprises reacting an olefin, oxygen, and hydrogen in the presence of a catalyst. The catalyst useful in the process of the invention comprises a titanium zeolite and a noble metal. Titanium zeolites comprise the class of zeolitic substances wherein titanium atoms are substituted for a portion of the silicon atoms in the lattice framework of a molecular sieve. Such substances are well known in the art.

Preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), "TS-3" (as described in Belgian Pat. No. 1,001,038), and titanium-MWW ("Ti-MWW", having a topology analogous to that of the MWW aluminosilicate zeolites). Titanium-containing molecular sieves having framework structures isomorphous to zeolite beta, mordenite, ZSM-48, ZSM-12, SBA-15, TUD, HMS, and MCM-41 are also suitable for use. TS-1 and Ti-MWW are particularly preferred. Ti-MWW zeolite is most preferred. Ti-MWW, and its production, is well known in the art. See for example, U.S. Pat. No. 6,759,540 and Wu et al., J. Phys. Chem. B, 2001, 105, p. 2897.

The catalyst employed in the process of the invention also comprises a noble metal. The noble metal is preferably incorporated into the catalyst by supporting the noble metal on the titanium zeolite to form a noble metal-containing titanium zeolite, or alternatively, the noble metal may be first supported on a carrier such as an inorganic oxide, day, carbon, or organic polymer resins, or the like, and then physically mixed with the titanium zeolite. There are no particular restrictions regarding the choice of noble metal compound used as the source of the noble metal. For example, suitable compounds include the nitrates, sulfates, halides (e.g., chlorides, bromides), carboxylates (e.g. acetate), and amine complexes of noble metals.

A preferred catalyst useful in the process of the invention is a noble metal-containing titanium zeolite. Such catalysts typically comprise a noble metal (such as palladium, gold, platinum, silver, iridium, ruthenium, osmium, or combinations thereof) supported on a titanium zeolite. Noble metal-containing titanium zeolites are well known in the art and are described, for example, in JP 4-352771 and U.S. Pat. Nos. 5,859,265 and 6,555,493, the teachings of which are incorporated herein by reference in their entirety. The noble metal-containing titanium zeolites may contain a mixture of noble metals. Preferred noble metal-containing titanium zeolites comprise palladium and a titanium zeolite; palladium, gold, and a titanium zeolite; or palladium, platinum, and titanium zeolite.

The typical amount of noble metal present in the noble metal-containing titanium-MWW zeolite will be in the range of from about 0.001 to 20 weight percent, preferably 0.005 to 10 weight percent, and particularly 0.01 to 5 weight percent.

Another preferred catalyst useful in the process of the invention is a catalyst mixture comprising a titanium zeolite and a supported noble metal catalyst. The supported noble metal catalyst comprises a noble metal and a carrier. The carrier is preferably a porous material. Carriers are well-known in the art. For instance, the carrier can be inorganic oxides, clays, carbon, and organic polymer resins. Preferred inorganic oxides include oxides of Group 2, 3, 4, 5, 6, 13, or 14 elements. Particularly preferred inorganic oxide carriers include silica, alumina, silica-aluminas, titania, zirconia, niobium oxides, tantalum oxides, molybdenum oxides, tungsten oxides, amorphous titania-silica, amorphous zirconia-silica, amorphous niobia-silica, and the like. The carrier may be a zeolite, but is not a titanium zeolite. Preferred organic polymer resins include polystyrene, styrene-divinylbenzene copolymers, crosslinked polyethyleneimines, and polybenzimidizole. Suitable carriers also include organic polymer resins grafted onto inorganic oxide carriers, such as polyethylenimine-silica. Preferred carriers also include carbon. Particularly preferred carriers include carbon, titania, zirconia, niobia, silica, alumina, silica-alumina, tantalum oxide, molybdenum oxide, tungsten oxide, titania-silica, zirconia-silica, niobia-silica, and mixtures thereof.

Preferably, the carrier has a surface area in the range of about 1 to about 700 $m^2/g$, most preferably from about 10 to about 500 $m^2/g$. Preferably, the pore volume of the carrier is in the range of about 0.1 to about 4.0 mL/g, more preferably from about 0.5 to about 3.5 mL/g, and most preferably from about 0.8 to about 3.0 mL/g. Preferably, the average particle size of the carrier is in the range of about 0.1 µm to about 0.5 inch, more preferably from about 1 µm to about 0.25 inch, and most preferably from about 10 µm to about 1/16 inch. The preferred particle size is dependent upon the type of reactor that is used, for example, larger particle sizes are preferred for a fixed bed reaction. The average pore diameter is typically in the range of about 10 to about 1000 Å, preferably about 20 to about 500 Å, and most preferably about 50 to about 350 Å.

The supported noble metal catalyst also contains a noble metal. While any of the noble metals can be utilized (i.e., gold, silver, platinum, palladium, iridium, ruthenium, osmium), either alone or in combination, palladium, platinum, gold, a palladium/platinum, or a palladium/gold combination are particularly desirable. Palladium is most preferred.

Typically, the amount of noble metal present in the supported catalyst will be in the range of from 0.01 to 10 weight percent, preferably 0.01 to 4 weight percent. There are no particular restrictions regarding the choice of noble metal compound or complex used as the source of noble metal in the supported catalyst. For example, suitable compounds include the nitrates, sulfates, halides (e.g., chlorides, bromides), carboxylates (e.g. acetate), oxides, and amine complexes of the noble metal.

Any suitable method may be used for the incorporation of the noble metal into the catalyst. For example, the noble metal may be supported on the titanium zeolite or the carrier by impregnation, ion-exchange, or incipient wetness techniques with for example, palladium tetraammine chloride.

After noble metal incorporation, the noble metal-containing titanium or supported noble metal catalyst is recovered. Suitable catalyst recovery methods include filtration and washing, rotary evaporation and the like. The catalyst is typically dried prior to use in epoxidation. The drying temperature is preferably from about 50° C. to about 200° C. The catalyst may additionally comprise a binder or the like and may be molded, spray dried, shaped or extruded into any desired form prior to use in epoxidation.

After noble metal-containing titanium or supported noble metal catalyst formation, the catalyst may be optionally thermally treated in a gas such as nitrogen, helium, vacuum, hydrogen, oxygen, air, or the like. The thermal treatment temperature is typically from about 20° C. to about 800° C. It is preferred to thermally treat the catalyst in the presence of an oxygen-containing gas at a temperature from about 200° C. to 700° C., and optionally reduce the catalyst in the presence of a hydrogen-containing gas at a temperature from about 20° C. to 600° C.

In the epoxidation process of the invention, the catalyst may be used as a powder or as a large particle size solid. If a noble metal-containing titanium zeolite is used, the noble metal-containing zeolite may be used as a powder but is preferably spray dried, pelletized or extruded prior to use in epoxidation. If spray dried, pelletized or extruded, the noble metal-containing titanium zeolite may additionally comprise a binder or the like and may be molded, spray dried, shaped or extruded into any desired form prior to use in epoxidation. The noble metal-containing titanium zeolite may also be encapsulated in polymer as described in U.S. Pat. No. 7,030,255, the teachings of which are incorporated herein by reference in their entirety. If a catalyst mixture of titanium zeolite and supported noble metal catalyst is used, the titanium zeolite and supported catalyst may be pelletized or extruded together, or encapsulated in polymer, prior to use in epoxidation, as described above.

The epoxidation process of the invention comprises contacting an olefin, oxygen, and hydrogen in a solvent comprising acetonitrile in the presence of the quinone-acid salt and the catalyst. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$-$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

Oxygen and hydrogen are also required for the epoxidation process. Although any sources of oxygen and hydrogen are suitable, molecular oxygen and molecular hydrogen are preferred.

The epoxidation process of the invention is carried out in the liquid (which includes supercritical or subcritical) phase in the presence of a solvent comprising acetonitrile. The solvent may preferably comprise co-solvents such as water. It is particularly preferable to use a mixture of acetonitrile and water.

The epoxidation process of the invention also employs one or more quinone-acid salt. A quinone-acid salt compound is a quinone compound that is substituted with at least one acid salt group. The quinone compound may be a quinone or hydroquinone. The quinone compound is preferably an anthraquinone, a phenanthrenequinone, a napthoquinone, an anthrahydroquinone, a naphthohydroquinone, or a phenanthrahydroquinone. More preferably, the quinone compound is preferably an anthraquinone, a phenanthrenequinone, or a napthoquinone. The preferred acid salt group is preferably an alkali metal or an ammonium or alkylammonium salt of a sulfonate, carboxylate, or phosphonate. Preferred alkylammoniums include tetramethylammonium, tetraethylammonium, and tetrabutylammonium cations. Preferred quinone-acid salts include sodium anthraquinone-2-sulfonate and sodium naphthoquinone-2-sulfonate. Most preferably, the quinone-acid salt is sodium anthraquinone-2-sulfonate.

The quinone-acid salt will typically be added to the reaction mixture along with the solvent. The amount of quinone-acid salt in the reaction mixture is preferably in the range of from 0.002 molar to 1 molar, and most preferably from about 0.02 molar to 0.2 molar.

Epoxidation according to the invention is carried out at a temperature effective to achieve the desired olefin epoxidation, preferably at temperatures in the range of 0-250° C., more preferably, 20-100° C. The molar ratio of hydrogen to oxygen can usually be varied in the range of $H_2:O_2=1:10$ to 5:1 and is especially favorable at 1:5 to 2:1. The molar ratio of oxygen to olefin is usually 2:1 to 1:20, and preferably 1:1 to 1:10. A carrier gas may also be used in the epoxidation process. As the carrier gas, any desired inert gas can be used. The molar ratio of olefin to carrier gas is then usually in the range of 100:1 to 1:10 and especially 20:1 to 1:10.

As the inert gas carrier, noble gases such as helium, neon, and argon are, suitable in addition to nitrogen and carbon dioxide. Saturated hydrocarbons with 1-8, especially 1-6, and preferably with 1-4 carbon atoms, e.g., methane, ethane, propane, and n-butane, are also suitable. Nitrogen and saturated $C_1$-$C_4$ hydrocarbons are the preferred inert carrier gases. Mixtures of the listed inert carrier gases can also be used.

Specifically in the epoxidation of propylene, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

The process of the invention preferably employs a buffer. The buffer will typically be added to the solvent to form a buffer solution. The buffer solution is employed in the reaction to inhibit the formation of glycols or glycol ethers during epoxidation. Buffers are well known in the art.

Buffers useful in this invention include any suitable salts of oxyacids, the nature and proportions of which in the mixture, are such that the pH of their solutions may preferably range from 3 to 12, more preferably from 4 to 10 and most preferably from 5 to 9. Suitable salts of oxyacids contain an anion and cation. The anion portion of the salt may include anions such as phosphate, carbonate, bicarbonate, carboxylates (e.g., acetate, phthalate, and the like), citrate, borate, hydroxide, silicate, aluminosilicate, or the like. The cation portion of the salt may include cations such as ammonium, alkylammoniums (e.g., tetraalkylammoniums, pyridiniums, and the like), alkali metals, alkaline earth metals, or the like. Cation examples include $NH_4$, $NBu_4$, $NMe_4$, Li, Na, K, Cs, Mg, and Ca cations. Buffers may preferably contain a combination of more than one suitable salt. Typically, the concentration of buffer in the solvent is from about 0.0001 M to about 1 M, preferably from about 0.0005 M to about 0.3 M. The buffer useful in this invention may also include the addition of ammonia gas or ammonium hydroxide to the reaction system. For instance, one may use a 0.1 to 1 N solution of ammonium hydroxide to balance the pH of the reaction system. More preferred buffers include alkali metal phosphate, ammonium phosphate, and ammonium hydroxide buffers.

The process of the invention may be carried out in a batch, continuous, or semi-continuous manner using any appropriate type of reaction vessel or apparatus such as a fixed-bed, transport bed, fluidized bed, stirred slurry, or CSTR reactor. The catalyst is preferably in the form of a suspension or fixed-bed. The process of the invention is preferably carried out at a temperature in the range of 0-150° C., more preferably, 20-120° C. It is advantageous to work at a pressure of 1 to 200 atmospheres, although the reaction can also be performed at atmospheric pressure.

The following examples merely illustrate the invention. Those skilled in the art will recognize many variations that are within the spirit of the invention and scope of the claims.

EXAMPLE 1

Preparation of Pd/Ti-MWW Catalyst

Ti-MWW Preparation: The gel is prepared following the procedure outlined in *J. Phys. Chem. B*, 2001, 105, p. 2897. Piperidine (876 g) is dissolved in deionized water (2259 g), stirred thoroughly for 10 minutes, and the solution is split into 2 equal parts. To the first part of the piperidine solution, tetrabutyl orthotitanate (TBOT; 57 g used when Si:Ti ratio is 39; 73.5 g used when Si:Ti ratio is 29; and 66 g used when Si:Ti ratio is 34) is added under air and the mixture stirred until the TBOT is dissolved to give a colorless solution. Fumed silica (198 g) is then gradually added to this solution with vigorous stirring, and then stirred for a further 1.5 hours to produce a titanium-containing gel. To the second part of the piperidine solution, boric acid (528 g) is slowly added under vigorous stirring until dissolved and then fumed silica (198 g) is gradually added with vigorous stirring, and then stirred for a further 1.5 hours to form a boric acid-containing gel. The titanium-containing gel is added to the boric acid-containing gel and stirred for an additional 1.5 hours to form a translucent gel.

The translucent gel is fed into stainless steel autoclaves without Teflon liners and the mixture heated at 130° C. for 24 hours, then 150° C. for another 24 hours, followed by heating at 170° C. for 10 days. The autoclave is then cooled and the solid is separated from the liquid by filtration either under nitrogen pressure or under vacuum. The resulting white solid is repeatedly rinsed with deionized water until the filtrate pH is about 10, the solid is air-dried, and then further dried at 60-80° C. in a vacuum oven for about 16 hours. The solid is then treated with nitric acid (2M $HNO_3$) at reflux for 24 hours (20 mL $HNO_3$ solution for every gram of solid). The solid product is filtered, washed with water until filtrate pH is greater than 4, and is then dried in a vacuum oven at 60-80° C. for 16 hours to form Ti-MWW.

Pd/Ti-MWW Preparation: Ti-MWW (50 g) is suspended in anhydrous acetone (400 mL), and a dark brown solution of palladium acetate (0.54 g) in anhydrous acetone (200 mL) is slowly added to the suspension at room temperature. Acetone is then removed by vacuum to yield a light yellow solid. The solids are vacuum dried at 60° C. and calcined in air in a muffle furnace by heating at 10° C./min to 110° C. for 4 hours and then at 2° C./min to 600° C. for 6 hours. The calcined solids are then transferred to a quartz tube and reduced with a 4 vol. % hydrogen in nitrogen stream at 100° C. for 1 hour (100 cc/hr), followed by nitrogen for 30 minutes while cooling from 100° C. to 30° C. to produce Pd/Ti-MWW catalyst. The Pd/Ti-MWW catalyst contains 0.48 wt % Pd.

EXAMPLE 2

Epoxidation Reactions

Preparation of Buffer Containing 9,10-Anthraquinone: Ammonium dihydrogen phosphate (1.478 g) in de-ionized water (771 g) is slowly added to a solution of 9,10-anthraquinone ("AQ", 0.375 g) in acetonitrile (1799 g), and then stirred at 450 rpm at room temperature for 20 minutes resulting in a clear, light green solution.

Preparation of Buffer Containing Sodium Salt of Anthraquinone-2-Sulfonic Acid: Ammonium dihydrogen phosphate (1.478 g) and anthraquinone-2-sulfonic acid, sodium salt ("AQSNa", 1.18 g) are dissolved in de-ionized water (771 g). Acetonitrile (1799 g) is then slowly added to yield a clear, pale yellow solution.

Comparative Epoxidation Run 2A: The reaction system consists of a 450-mL stainless steel CSTR type reactor. Gas and liquid feeds enter the reactor, and the vapor exits the reactor through a port at the top of the reactor, while the liquid exits through a filter which keeps the catalyst in the reactor. Pd/Ti-MWW catalyst (8 g) and the anthraquinone-containing buffer solution (211 g) are added to the reactor. The reactor is then charged to 600 psig (4137 kPa) with a feed gas consisting of 3.8 volume percent (vol. %) hydrogen, 4.4 vol. % oxygen, 6.7 vol. % propylene, 0.4 vol. % methane, and the balance nitrogen. The feed gases are passed continuously through the reactor at 2800 mL/min (measured at 23° C. and 1 atmosphere pressure) and the anthraquinone-containing buffer is continuously added to the reactor at the rate of 115 g/hr. The slurry in the reactor is heated to 60° C. under about 600 psig (4137 kPa), and is stirred at 800 rpm.

Propylene oxide and equivalents ("POE") are produced during the reaction. POE produced include propylene oxide ("PO") and the ring-opened products ("RO") propylene glycol and glycol ethers. The products coming out of the reactor (in both vapor and liquid phase) are analyzed by GC. The results of the GC analyses are used to calculate the selectivity of hydrogen to PO ("SHPO"), the selectivity of oxygen to PO ("SOPO"), the PO Rate (grams POE produced/gram of catalyst per hour), and volume productivity (grams PO produced/Liter per hour) shown in Table 1.

Epoxidation Run 2B: Epoxidation Run 2B is run according to the procedure of Comparative Run 2A, with the exception that the buffer used is the sodium salt of anthraquinone-2-sulfonic acid-containing buffer and the feed gas consists of 4 volume percent (vol. %) hydrogen, 4.4 vol. % oxygen, 6 vol. % propylene, 0.4 vol. % methane, and the balance nitrogen.

Epoxidation Run 2C: Epoxidation Run 2C is run according to the procedure of Epoxidation Run 2B, with the exception that the feed gas consists of 3.1 volume percent (vol. %) hydrogen, 4.4 vol. % oxygen, 6 vol. % propylene, 0.4 vol. % methane, and the balance nitrogen.

The results are shown in Table 1, and demonstrate that the use of a quinone-acid salt results in higher productivity while also increasing the propylene oxide selectivity from both hydrogen and oxygen.

TABLE 1

Epoxidation Results

| Run # | Modifier (Amount) | PO Rate [1] | SHPO (%) [2] | SOPO (%) [3] | Prod. [4] |
|---|---|---|---|---|---|
| 2A * | AQ (0.7 mmol) | 0.491 | 29 | 49 | 18.4 |
| 2B | AQSNa (1.4 mmol) | 0.544 | 38 | 68 | 20.5 |
| 2C | AQSNa (1.4 mmol) | 0.516 | 51 | 67 | 19.6 |

[1] PO Rate = grams POE produced/gram of catalyst per hour.
[2] SHPO (Sel. $H_2$ to PO) = rate of PO produced/rate of $H_2$ consumed.
[3] SOPO (Sel. $O_2$ to PO) = rate of PO produced/rate of $O_2$ consumed.
[4] Productivity = grams PO produced/Liter per hour.
* Comparative Example

We claim:

1. A process for producing an epoxide, which comprises reacting an olefin, oxygen, and hydrogen in a solvent comprising acetonitrile in the presence of a quinone-acid salt and a catalyst comprising a titanium zeolite and a noble metal.

2. The process of claim 1 wherein the noble metal is palladium.

3. The process of claim 1 wherein the titanium zeolite is a titanium-MWW zeolite.

4. The process of claim 1 wherein the noble metal is supported on the titanium zeolite.

5. The process of claim 1 wherein the noble metal is supported on a carrier.

6. The process of claim 5 wherein the carrier is selected from the group consisting of carbon, titania, zirconia, niobia, silica, alumina, silica-alumina, tantalum oxide, molybdenum oxide, tungsten oxide, titania-silica, zirconia-silica, niobia-silica, and mixtures thereof.

7. The process of claim 1 wherein the olefin is a $C_2$-$C_6$ olefin.

8. The process of claim 1 wherein the olefin is propylene.

9. The process of claim 1 wherein the quinone-acid salt is a quinone or hydroquinone compound that is substituted with at least one acid salt group.

10. The process of claim 9 wherein the quinone or hydroquinone compound is an anthraquinone, a phenanthrenequinone, or a napthaquinone, and the acid salt group is an alkali metal or an ammonium or alkylammonium salt of a sulfonate, carboxylate, or phosphonate.

11. The process of claim 9 wherein the quinone-acid salt is sodium anthraquinone-2-sulfonate.

12. The process of claim 1 wherein the solvent further comprises water.

* * * * *